United States Patent
Tang et al.

(10) Patent No.: US 10,294,203 B2
(45) Date of Patent: May 21, 2019

(54) ORGANIC COMPOUND AND ELECTRONIC DEVICE COMPRISING AN ORGANIC LAYER COMPRISING THE ORGANIC COMPOUND

(71) Applicants: Dow Global Technologies LLC, Midland, MI (US); Rohm and Haas Electronic Materials Korea Ltd., Cheonan (KR)

(72) Inventors: Zhengming Tang, Shanghai (CN); Chong Xing, Shanghai (CN); Shaoguang Feng, Shanghai (CN); Minrong Zhu, Shanghai (CN); Hua Ren, Shanghai (CN); Hong-Yeop Na, Seoul (KR); Yuchen Liu, Shanghai (CN); Robert J. Wright, Sugar Land, TX (US); David D. Devore, Midland, MI (US)

(73) Assignees: Dow Global Technologies LLC, Midland, MI (US); Rohm and Haas Electronic Materials Korea Ltd. (KR)

( * ) Notice: Subject to any disclaimer, the term of this patent is extended or adjusted under 35 U.S.C. 154(b) by 0 days.

(21) Appl. No.: 15/537,444

(22) PCT Filed: Nov. 11, 2015

(86) PCT No.: PCT/CN2015/094263
§ 371 (c)(1),
(2) Date: Jun. 19, 2017

(87) PCT Pub. No.: WO2016/101721
PCT Pub. Date: Jun. 30, 2016

(65) Prior Publication Data
US 2017/0334849 A1 Nov. 23, 2017

(30) Foreign Application Priority Data
Dec. 26, 2014 (WO) ................ PCT/CN2014/095088

(51) Int. Cl.
C07D 207/335 (2006.01)
C09K 11/06 (2006.01)

(52) U.S. Cl.
CPC .......... *C07D 207/335* (2013.01); *C09K 11/06* (2013.01); *C09K 2211/1007* (2013.01); *C09K 2211/1011* (2013.01); *C09K 2211/1029* (2013.01)

(58) Field of Classification Search
CPC .................................................... C07D 207/32
See application file for complete search history.

(56) References Cited

FOREIGN PATENT DOCUMENTS

| JP | 2007320925 A | 12/2007 | |
|---|---|---|---|
| WO | 2010004887 A1 | 1/2010 | |
| WO | WO-2010004887 A1 * | 1/2010 | .......... C07F 15/0033 |

OTHER PUBLICATIONS

P. Kuo et al., 63 Tetrahedron, 7086-7096 (Jul. 23, 2007).*
CAS Abstract WO2010004887 (2010).*
English Machine Translation WO2010004887 (2010).*
C-S Li et al., 75 Journal of Organic Chemistry, 4004-4013 (2010).*
W-J Kuo et al., 63 Tetrahedron (May 13, 2007).*
Kuo, et al., "Peripheral aryl-substituted pyrrole fluorophores for glassy blue-light-emitting diodes", Tetrahedron, vol. 63, pp. 7086-7096 (2007).
Li, et al., "Synthesis and Photophysical Properties of Pyrrole/Polycyclic Aromatic Units Hybrid Fluorophores", J. Org. Chem., vol. 75, pp. 4004-4013 (2010).

* cited by examiner

*Primary Examiner* — Alexander R Pagano
(74) *Attorney, Agent, or Firm* — S. Matthew Cairns

(57) ABSTRACT

An organic compound suitable for organic layers of electronic devices that show improved luminescent properties.

12 Claims, No Drawings

ORGANIC COMPOUND AND ELECTRONIC DEVICE COMPRISING AN ORGANIC LAYER COMPRISING THE ORGANIC COMPOUND

FIELD OF THE INVENTION

The present invention relates to an organic compound, and an electronic device comprising an organic layer comprising the organic compound.

INTRODUCTION

Organic light emitting diodes (OLEDs) are display devices that employ stacks of films containing organic aromatic compounds as electron transport layers (ETLs) and hole transport layers (HTLs). To compete with other displays such as liquid crystal displays (LCDs), it is important to develop materials with improved luminescent properties such as reduced driving voltage and/or increased luminous efficiency to minimize power consumption in OLED displays, especially for mobile applications where batteries are used as power sources. There have been tremendous amount of research to develop materials to reduce driving voltages and increase luminous efficiency, mostly for hole injection materials (HIMs), such as described in *Synthetic Metals*, 2009, 159, 69 and *J. Phys. D: Appl. Phys.* 2007, 40, 5553. For hole transport layers, traditionally used materials such as 4,4-N,N-bis-N-1-naphthyl-N-phenyl-amino-biphenyl (NPB) usually provide unsatisfactory luminescent properties. Thus, there remains a need for new compounds suitable for preparing hole transport layers of OLEDs which have improved luminescent properties than those comprising NPB-based hole transport layers.

Therefore, it is desirable to provide new compounds that are suitable to be used as hole transport materials capable of providing improved luminescent properties.

SUMMARY OF THE INVENTION

The present invention provides a novel organic compound, and an electronic device comprising an organic layer comprising the organic compound. The electronic device of the present invention shows better luminescent properties than devices comprising NPB as a hole transport material.

In a first aspect, the present invention provides an organic compound having the structure represented by Formula (1):

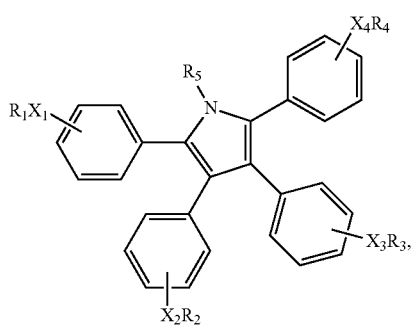

Formula (1)

wherein $X_1$ through $X_4$ are each independently a chemical bond, or each independently selected from the group consisting of a substituted or unsubstituted $C_6$-$C_{60}$ arylene and a substituted or unsubstituted $C_1$-$C_{60}$ heteroarylene; and $X_1$ through $X_4$ may each independently form fused rings with the phenyl rings they are bonded to;

$R_1$ through $R_4$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, a carbonyl, and an amino group substituted with a substituted or unsubstituted $C_6$-$C_{60}$ aryl or a substituted or unsubstituted $C_1$-$C_{60}$ heteroaryl; and at least one of $R_1$ through $R_4$ is an amino group substituted with a substituted or unsubstituted $C_6$-$C_{60}$ aryl or a substituted or unsubstituted $C_1$-$C_{60}$ heteroaryl; and $R_5$ is selected from the group consisting of hydrogen, deuterium, a substituted or unsubstituted $C_1$-$C_{50}$ alkyl, a substituted or unsubstituted $C_1$-$C_{50}$ alkoxycarbonyl, a substituted or unsubstituted $C_6$-$C_{60}$ aryl, and a substituted or unsubstituted $C_1$-$C_{60}$ heteroaryl.

In a second aspect, the present invention provides an electronic device comprising an organic layer, wherein the organic layer comprises the organic compound of the first aspect.

DETAILED DESCRIPTION OF THE INVENTION

The organic compound of the present invention may have the structure represented by Formula (1):

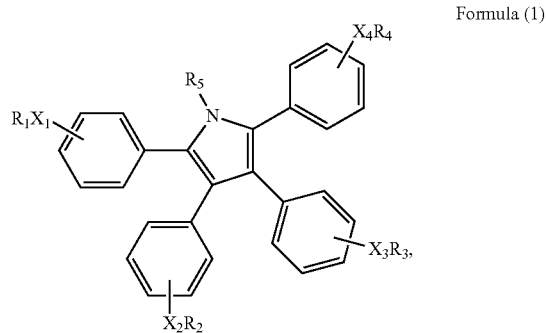

Formula (1)

In Formula (1), $R_1$, $R_2$, $R_3$, and $R_4$ may be the same or different. One or more of $R_1$ through $R_4$ is an amino group substituted with a substituted or unsubstituted $C_6$-$C_{60}$ aryl or a substituted or unsubstituted $C_1$-$C_{60}$ heteroaryl (hereinafter "substituted amino group"). The substituted amino group may have the structure of Formula (A):

Formula (A)

wherein $Ar_1$ and $Ar_2$ are each independently selected from the group consisting of a substituted or unsubstituted $C_6$-$C_{60}$ aryl and a substituted or unsubstituted $C_1$-$C_{60}$ heteroaryl. In some embodiments, only one of $R_1$ through $R_4$ is the substituted amino group, and the remaining three of $R_1$ through $R_4$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl. Preferably, only one of $R_1$ through $R_4$ is the substituted amino group, and the remaining $R_1$ through $R_4$ are each independently selected from the groups consisting of hydrogen, phenyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl. The anthryl may be 1-anthryl, 2-anthryl or 9-anthryl. The fluorenyl may be any one of 1-fluorenyl, 2-fluorenyl, 3-fluorenyl, 4-fluorenyl and 9-fluorenyl. In some embodiments, only $R_3$ or $R_4$ is the substituted amino group.

The organic compound of the present invention may have the structure represented by Formula (2):

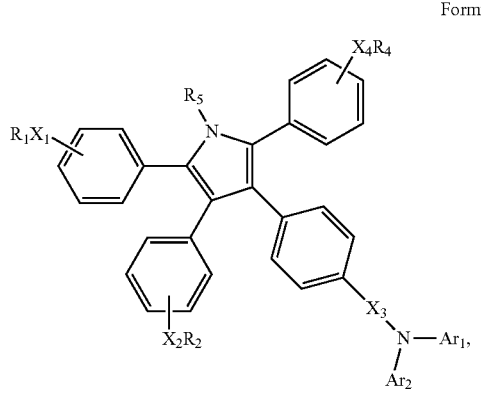

Formula (2)

wherein $Ar_1$ and $Ar_2$ are each independently selected from the group consisting of a substituted or unsubstituted $C_6$-$C_{60}$ aryl and a substituted or unsubstituted $C_1$-$C_{60}$ heteroaryl;

$R_1$, $R_2$ and $R_4$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{50}$ aryloxy, a substituted or unsubstituted $C_6$-$C_{60}$ arylthio, a substituted or unsubstituted $C_1$-$C_{60}$ heteroaryl, a halogen, a cyano, a hydroxyl, a carbonyl, and an amino group substituted with a substituted or unsubstituted $C_6$-$C_{60}$ aryl or a substituted or unsubstituted $C_1$-$C_{60}$ heteroaryl; and $R_5$ and $X_1$ through $X_4$ are as previously defined with reference to Formula (1). Preferably, $R_1$, $R_2$, and $R_4$ are each independently selected from hydrogen or a substituted or unsubstituted $C_6$-$C_{60}$ aryl. Preferably, $X_1$, $X_2$, $X_3$, and $X_4$ are each a chemical bond. Chemical bond herein means that two groups bonded to the chemical bond are directly linked to each other. For example, when $X_1$ is a chemical bond, it means that $R_1$ is directly linked to the phenyl ring.

Preferably, in Formula (2), $R_1$, $R_2$ and $R_4$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{50}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl.

The organic compound of the present invention may have the structure represented by Formula (3):

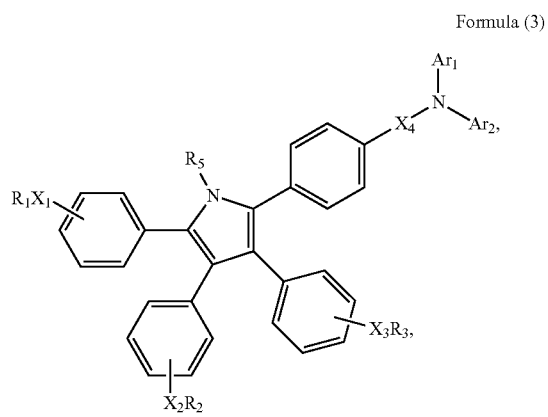

Formula (3)

wherein $Ar_1$ and $Ar_2$ are each independently selected from the group consisting of a substituted or unsubstituted $C_6$-$C_{60}$ aryl and a substituted or unsubstituted $C_1$-$C_{60}$ heteroaryl;

$R_1$, $R_2$, and $R_3$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{50}$ aryloxy, a substituted or unsubstituted $C_6$-$C_{50}$ arylthio, a substituted or unsubstituted $C_1$-$C_{60}$ heteroaryl, a halogen, a cyano, a hydroxyl, a carbonyl, and an amino group substituted with a substituted or unsubstituted $C_6$-$C_{60}$ aryl or a substituted or unsubstituted $C_1$-$C_{60}$ heteroaryl; and $R_5$ and $X_1$ through $X_4$ are as previously defined with reference to Formula (1). Preferably, $X_1$, $X_2$, $X_3$, and $X_4$ are each a chemical bond. Preferably, $R_1$ $R_2$, and $R_3$ are each independently selected from hydrogen or a substituted or unsubstituted $C_6$-$C_{60}$ aryl.

Preferably, in Formula (3), $R_1$, $R_2$, and $R_3$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{50}$ aryloxy, a substituted or unsubstituted $C_6$-$C_{50}$ arylthio, a substituted or unsubstituted $C_1$-$C_{60}$ heteroaryl, a halogen, a cyano, a hydroxyl, and a carbonyl.

In some embodiments, the organic compound of the present invention has the structure represented by Formula (4):

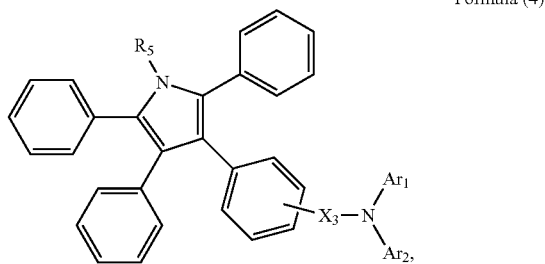

Formula (4)

wherein Ar$_1$ and Ar$_2$ are each independently selected from the group consisting of a substituted or unsubstituted C$_6$-C$_{60}$ aryl and a substituted or unsubstituted C$_1$-C$_{60}$ heteroaryl; and R$_5$ and X$_3$ are as previously defined with reference to Formula (1).

In some embodiments, the organic compound of the present invention has the structure represented by Formula (4-I):

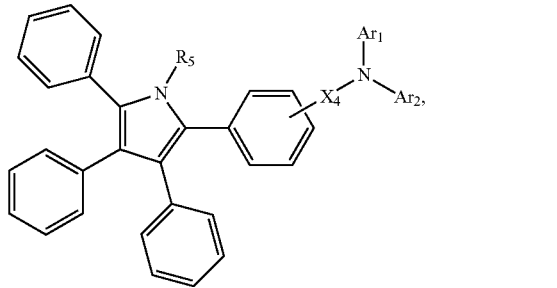

Formula (4-I)

wherein Ar$_2$ and Ar$_2$ are each independently selected from the group consisting of a substituted or unsubstituted C$_6$-C$_{60}$ aryl and a substituted or unsubstituted C$_1$-C$_{60}$ heteroaryl; and R$_5$ and X$_4$ are as previously defined with reference to Formula (1).

In Formula (1), (2), (3), (4), and (4-I), R$_5$ can be a substituted or unsubstituted C$_1$-C$_{30}$ alkyl, C$_1$-C$_{20}$ alkyl, C$_1$-C$_{10}$ alkyl, C$_1$-C$_5$ alkyl, or C$_1$-C$_3$ alkyl; a substituted or unsubstituted C$_3$-C$_{50}$ cycloalkyl, C$_4$-C$_{30}$ cycloalkyl, C$_4$-C$_{20}$ cycloalkyl, or C$_4$-C$_{12}$ cycloalkyl; a substituted or unsubstituted C$_6$-C$_{60}$ aryl, C$_6$-C$_{30}$ aryl, C$_6$-C$_{20}$ aryl, or C$_6$-C$_{12}$ aryl; or a substituted or unsubstituted C$_1$-C$_{60}$ heteroaryl, C$_1$-C$_{30}$ heteroaryl, C$_2$-C$_{20}$ heteroaryl, or C$_4$-C$_{12}$ heteroaryl. Preferably, R$_5$ is selected from
—CH$_3$, —CH$_2$CH$_3$,

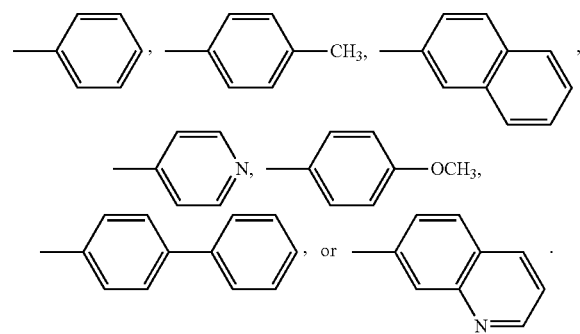

X$_1$, X$_2$, X$_3$ and X$_4$ in Formula (1), (2), and (3); X$_3$ in Formula (4); and X$_4$ in Formula (4-I); respectively, are each independently a chemical bond, or each independently selected from a substituted or unsubstituted C$_6$-C$_{60}$ arylene, C$_6$-C$_{30}$ arylene, C$_6$-C$_{20}$ arylene, or C$_6$-C$_{12}$ arylene; or a substituted or unsubstituted C$_1$-C$_{60}$ heteroarylene, C$_1$-C$_{30}$ heteroarylene, C$_2$-C$_{20}$ heteroarylene, or C$_4$-C$_{12}$ heteroarylene. Examples of X$_1$ through X$_4$ include

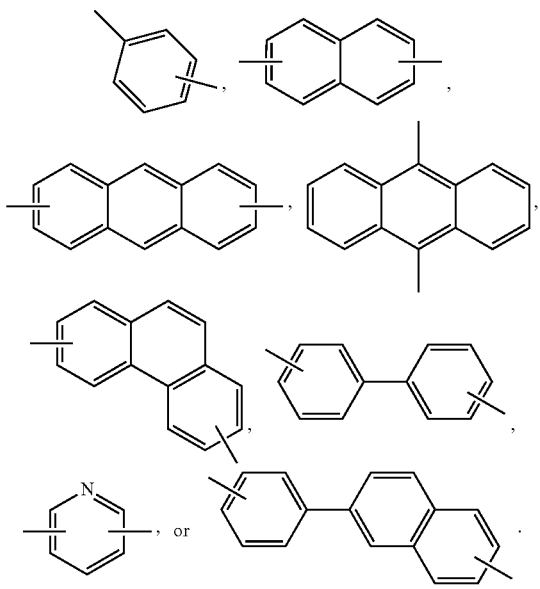

In some embodiments, X$_1$, X$_2$, X$_3$, and X$_4$ are each a chemical bond.

R$_1$ through R$_4$ in Formula (1); R$_1$, R$_2$ and R$_4$ in Formula (2); and R$_1$, R$_2$ and R$_3$ in Formula (3), respectively, may be each independently selected from the group consisting of hydrogen; deuterium; a substituted or unsubstituted C$_1$-C$_{50}$ alkyl, C$_1$-C$_{30}$ alkyl, C$_1$-C$_{20}$ alkyl, or C$_1$-C$_{10}$ alkyl; a substituted or unsubstituted C$_6$-C$_{60}$ aryl, C$_6$-C$_{30}$ aryl, C$_6$-C$_{20}$ aryl, or C$_6$-C$_{12}$ aryl; a substituted or unsubstituted C$_1$-C$_{60}$ heteroaryl, C$_1$-C$_{30}$ heteroaryl, C$_2$-C$_{20}$ heteroaryl, or C$_4$-C$_{12}$ heteroaryl; an alkoxy or an alkoxycarbonyl containing a C$_1$-C$_{50}$ alkyl, C$_1$-C$_{30}$ alkyl, C$_1$-C$_{20}$ alkyl, or C$_1$-C$_{10}$ alkyl; a substituted or unsubstituted C$_6$-C$_{50}$ aryloxy, C$_6$-C$_{30}$ aryloxy, C$_6$-C$_{20}$ aryloxy, or C$_6$-C$_{10}$ aryloxy; a substituted or unsubstituted C$_6$-C$_{60}$ arylthio, C$_6$-C$_{30}$ arylthio, C$_6$-C$_{20}$ arylthio, or C$_6$-C$_{12}$ arylthio; a halogen such as F, Cl, Br or I; a cyano; a hydroxyl; and a carbonyl. Preferably, these groups are each independently selected from a substituted or unsubstituted C$_6$-C$_{60}$ aryl, C$_6$-C$_{30}$ aryl, C$_6$-C$_{20}$ aryl, or C$_6$-C$_{12}$ aryl; hydrogen; or a halogen; and more preferably, each independently selected from hydrogen, F, methyl, phenyl, naphthyl, or biphenyl. In some embodiments, at least two of R$_1$ through R$_4$ are hydrogen, and more preferably, three of R$_1$ through R$_4$ are hydrogen.

In Formula (A), (2), (3), (4), and (4-I), respectively, Ar$_1$ and Ar$_2$ are each independently selected from a substituted or unsubstituted C$_6$-C$_{60}$ aryl, C$_6$-C$_{30}$ aryl, C$_6$-C$_{20}$ aryl, or C$_6$-C$_{15}$ aryl; or a substituted or unsubstituted C$_1$-C$_{60}$ heteroaryl, C$_1$-C$_{30}$ heteroaryl, C$_2$-C$_{20}$ heteroaryl, or C$_4$-C$_{12}$ heteroaryl. Preferably, Ar$_1$ and Ar$_2$ are each a substituted or unsubstituted C$_6$-C$_{60}$ aryl, C$_6$-C$_{30}$ aryl, C$_6$-C$_{20}$ aryl, or C$_6$-C$_{15}$ aryl. More preferably, Ar$_1$ and Ar$_2$ are each independently a substituted or unsubstituted C$_{12}$-C$_{30}$ aryl.

The substituted amino group, that is, one or more of $R_1$ through $R_4$ in Formula (1), or

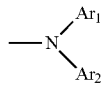

in Formula (A), (2), (3), (4), or (4-I) may have the structures represented by Formula (5a), (5b), or (5c):

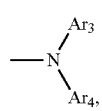

Formula (5a)

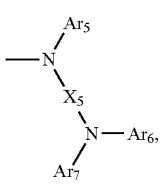

Formula (5b)

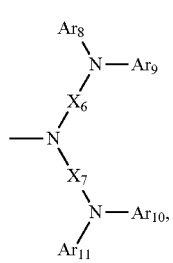

Formula (5c)

wherein $Ar_3$ and $Ar_4$ are each independently a unsubstituted $C_6$-$C_{60}$ aryl, $Ar_5$ through $Ar_7$ are each independently a unsubstituted $C_6$-$C_{40}$ aryl, $Ar_8$ through $Ar_{11}$ are each independently a unsubstituted $C_6$-$C_{30}$ aryl, and $X_5$ through $X_7$ are each independently selected from the group consisting of a substituted or unsubstituted $C_6$-$C_{60}$ arylene and a substituted or unsubstituted $C_1$-$C_{60}$ heteroarylene; and $X_5$ through $X_7$ may be each independently selected from a substituted or unsubstituted $C_6$-$C_{60}$ arylene, $C_6$-$C_{30}$ arylene, $C_6$-$C_{20}$ arylene, or $C_6$-$C_{12}$ arylene; or a substituted or unsubstituted $C_1$-$C_{60}$ heteroarylene, $C_1$-$C_{30}$ heteroarylene, $C_2$-$C_{20}$ heteroarylene, or $C_4$-$C_{12}$ heteroarylene. Preferably, $Ar_3$ through $Ar_{11}$ may be each a unsubstituted $C_6$-$C_{30}$ aryl, $C_6$-$C_{20}$ aryl, $C_6$-$C_{15}$ aryl, or $C_6$-$C_{12}$ aryl. Preferably, at least one of $R_1$ and $R_4$ has the structure of Formula (5a). Examples of suitable substituted amino groups in the present invention include the following structures (5-1) through (5-9):

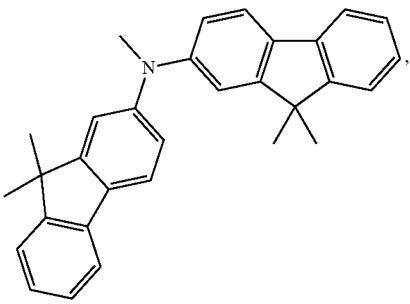

(5-1)

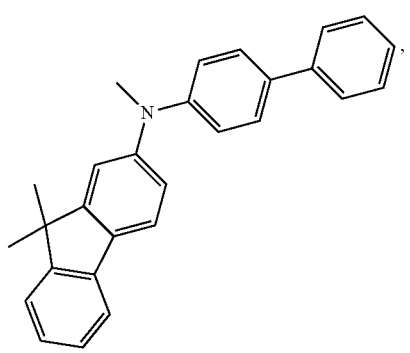

(5-2)

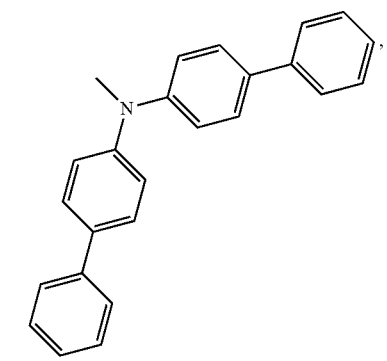

(5-3)

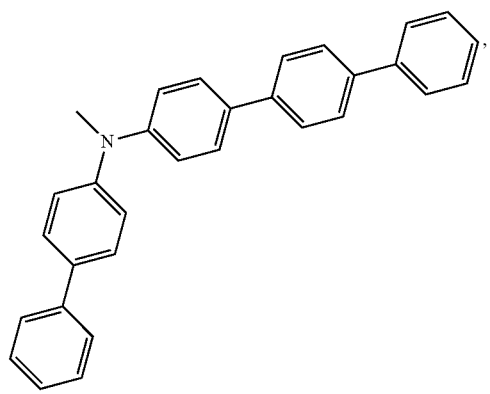

(5-4)

(5-5)
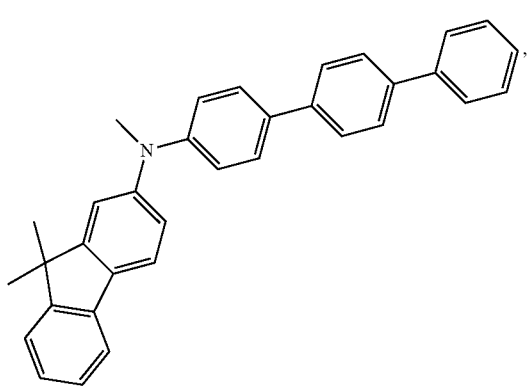
(5-6)
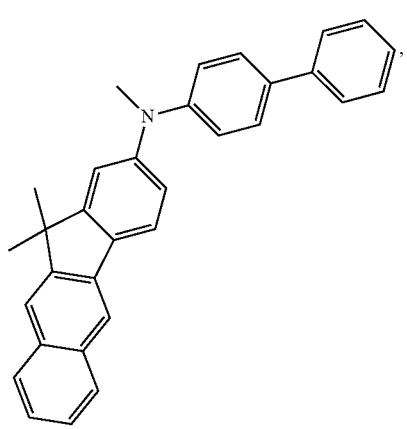
(5-7)
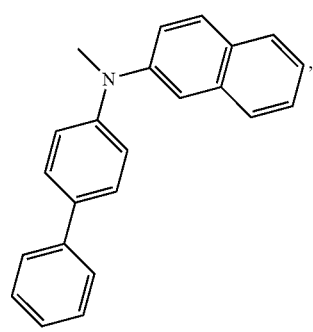
(5-8)
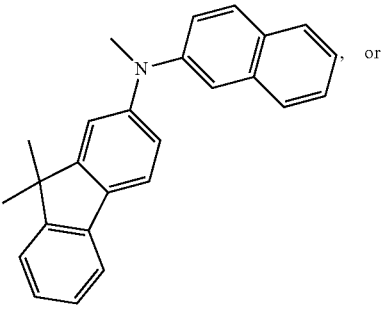
, or
(5-9)
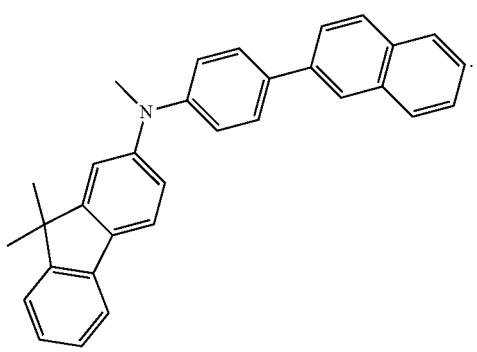
In some embodiments, the organic compound of the present invention is selected from the following compounds (1) through (16):
(1)
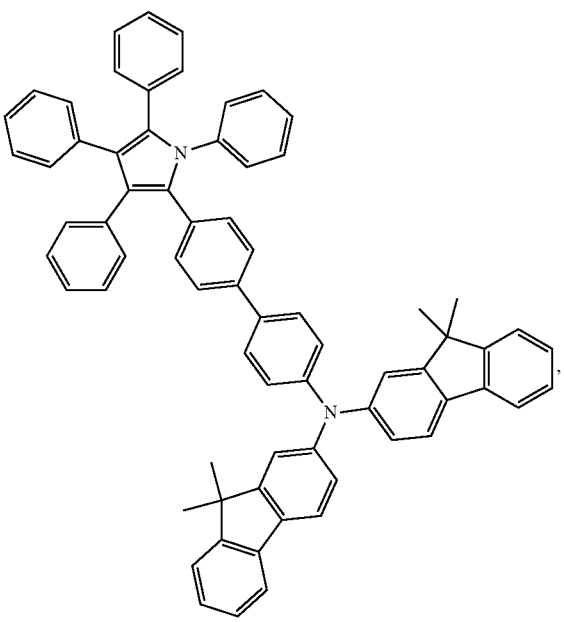

(2)
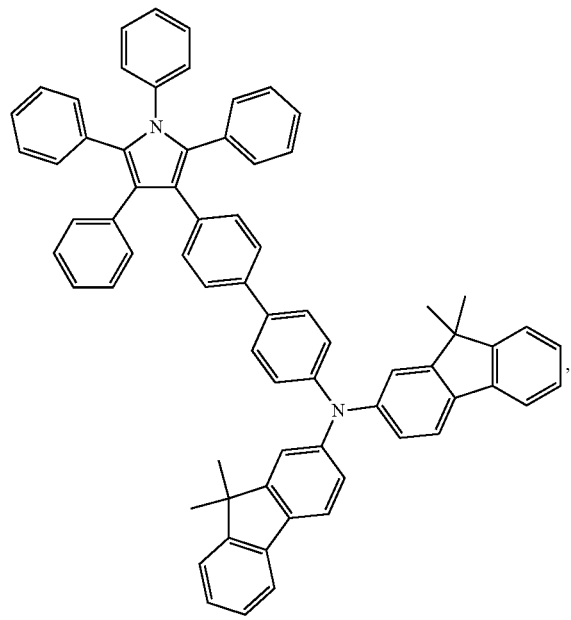
(3)
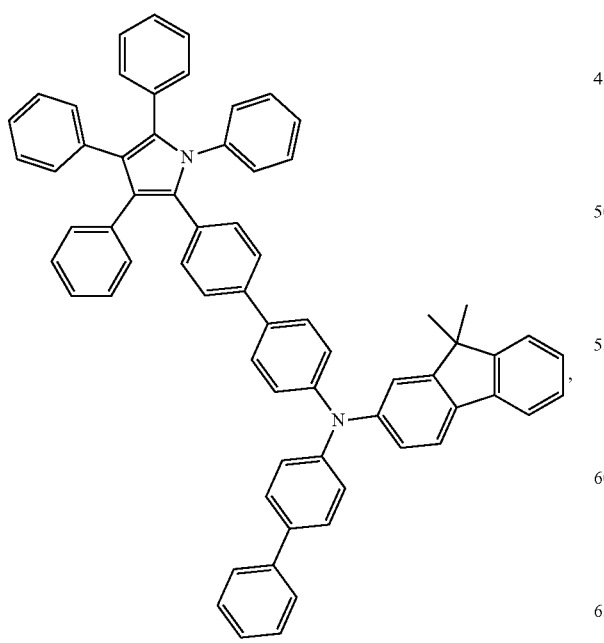
(4)
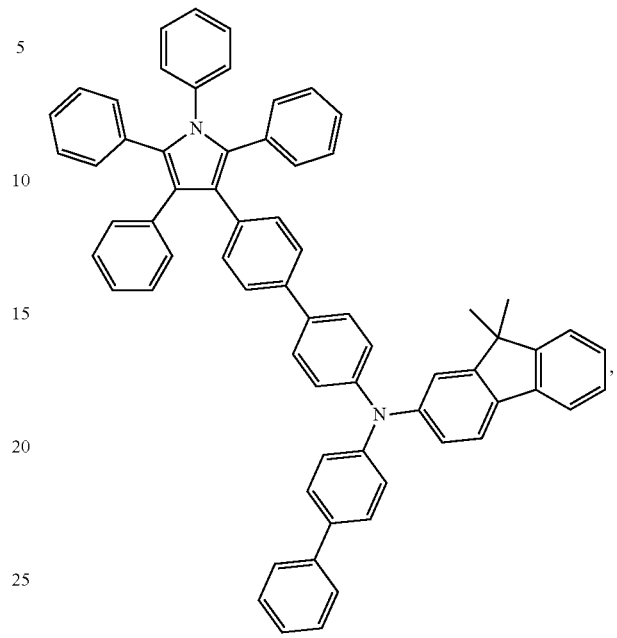
(5)
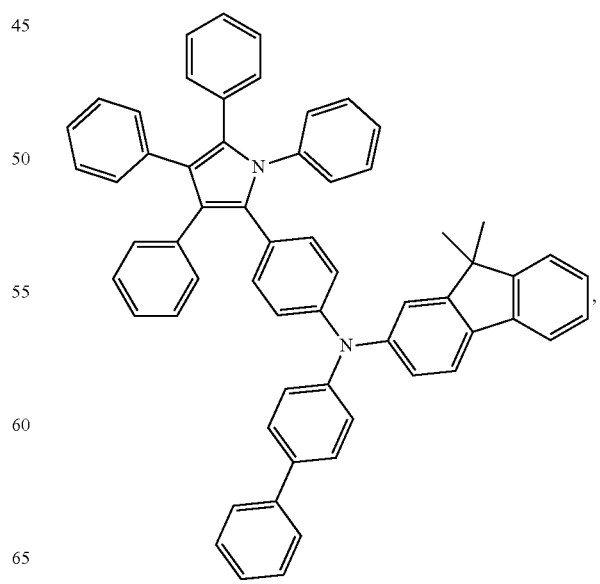

(6)
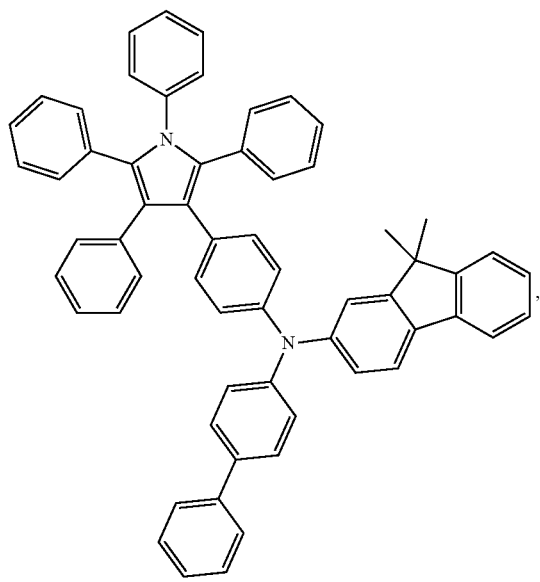
(8)
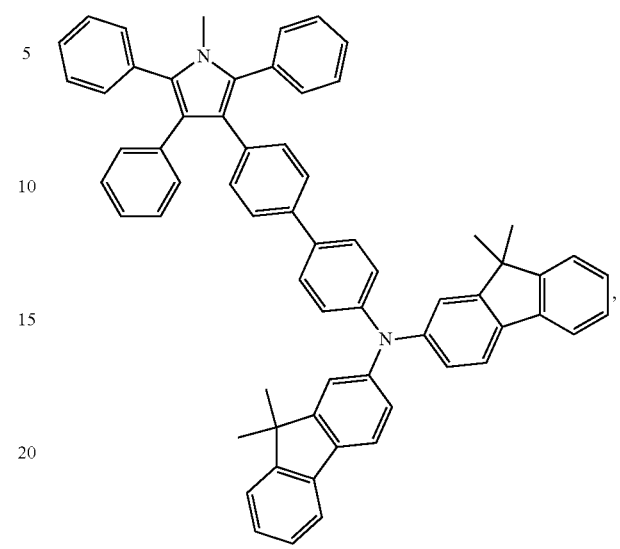
(7)
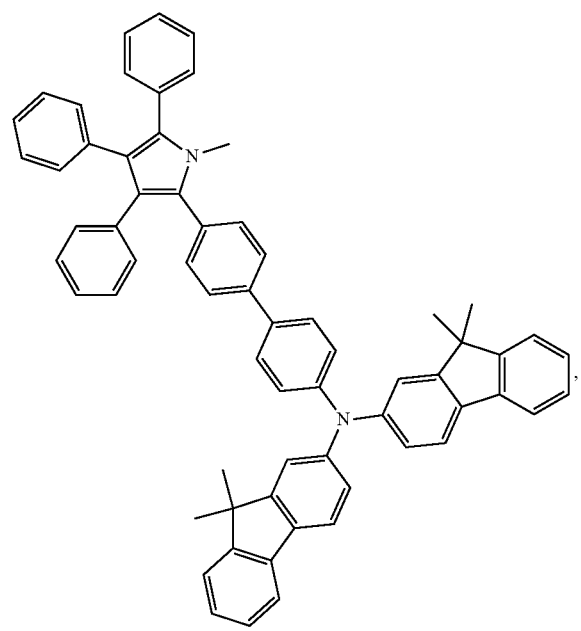
(9)
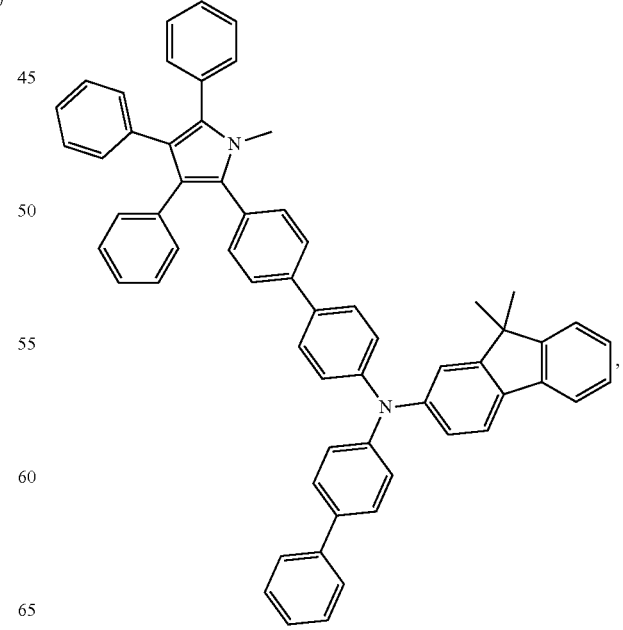

(10)
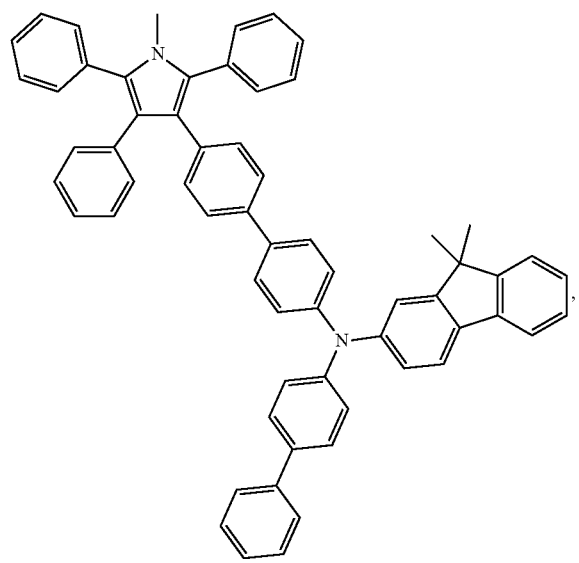
(11)
(12)
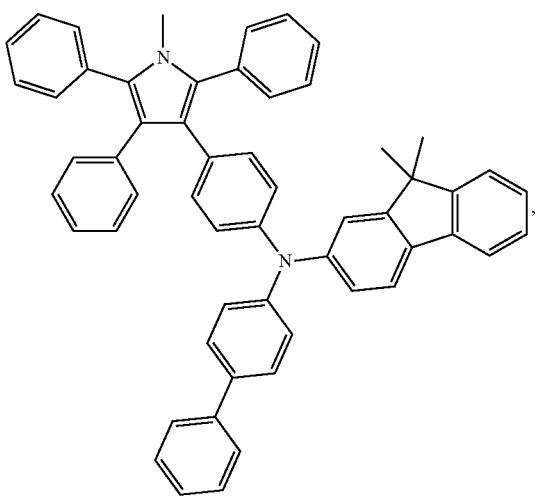
(13)
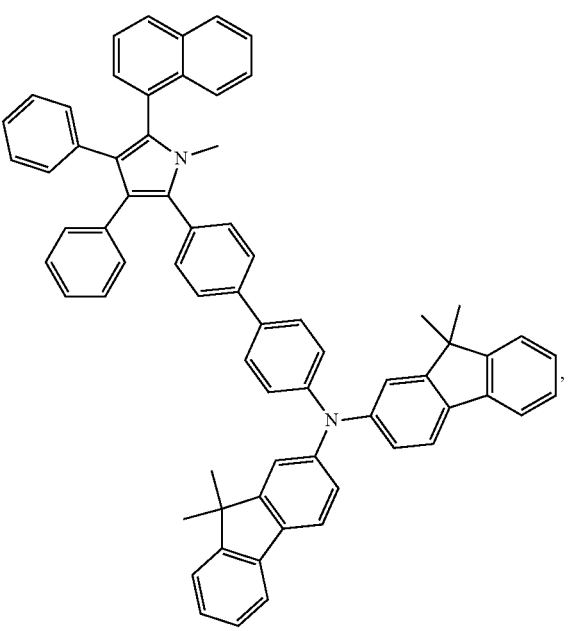

-continued

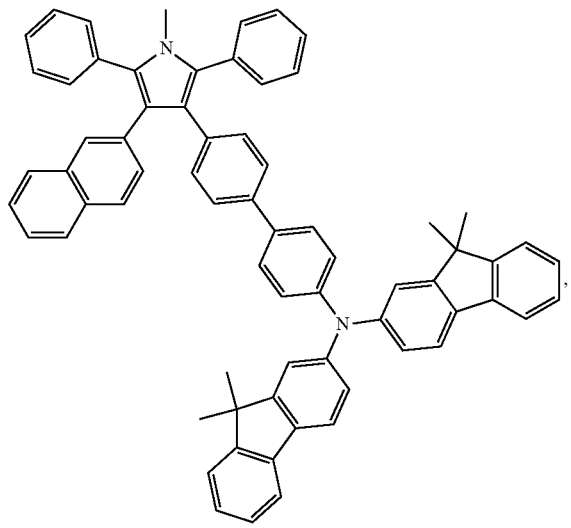
(14)

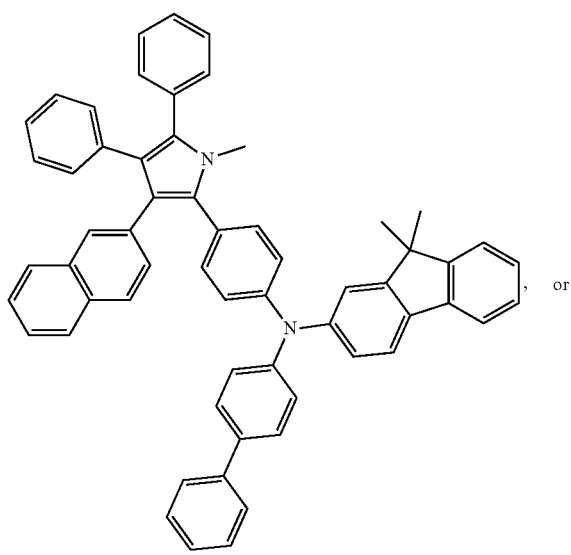
(15)

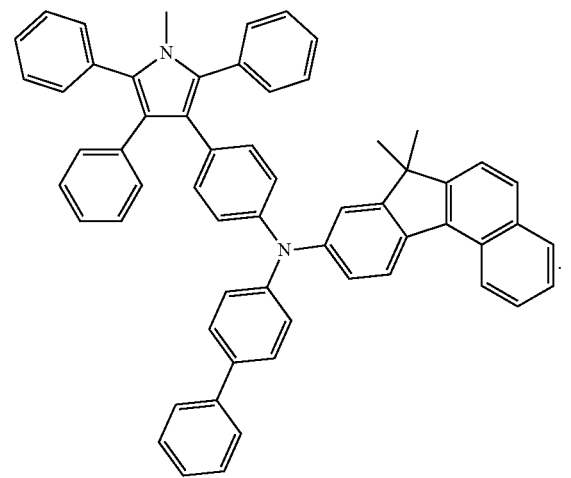
(16)

The organic compound of the present invention may have a molecular weight of 500 g/mole or more, 600 g/mole or more, or even 700 g/mole or more, and at the same time, 1,000 g/mole or less, 900 g/mole or less, or even 800 g/mole or less.

The organic compound of the present invention may have the highest occupied molecular orbital (HOMO) level from −4.50 to −5.00 electronvolts (eV) or from −4.60 to −4.80 eV, as determined according to the test method described in the Examples section below.

The organic compound of the present invention may have the lowest unoccupied molecular orbital (LUMO) level from 0.00 to −1.10 eV or from 0.00 to −0.90 eV, as determined according to the test method described in the Examples section below.

The organic compound of the present invention may have a triplet energy of from 2.10 to 3.30 eV or from 2.60 to 3.30 eV, as determined according to the test method described in the Examples section below.

The organic compound of the present invention may have a glass transition temperature ($T_g$) of 110° C. or higher, 130° C. or higher, or 150° C. or higher, and at the same time, 250° C. or lower, 220° C. or lower, or even 200° C. or lower, as measured according to the test method described in the Examples section below.

The organic compound of the present invention may have a decomposition temperature ($T_d$) at 5% weight loss of 300° C. or higher, 350° C. or higher, or 400° C. or higher, and at the same time, 650° C. or lower, 600° C. or lower, or even 550° C. or lower, as measured according to the test method described in the Examples section below.

The organic compound of the present invention may be prepared by conventional methods in the art, for example, as shown in Scheme 1 below to prepare the organic compound having the structure represented by Formula (2). A derivative of 1,4-unsaturated ketone may react with a derivative of benzaldehyde through a Stetter reaction to give a diketone derivative of Structure 1. Examples of suitable catalysts for the Stetter reaction include cyanide salts such as sodium cyanide and thiazolium salts such as 3-ethyl-5-(2-hydroxyethyl)-4-methylthiazolium bromide and 3-benzyl-5-(2-hydroxyethyl)-4-methylthiazolium Chloride. Then the compound of Structure 1 may react with an amine with the structure of $R_5NH_2$. The resultant compound of Structure 2 may react with N-bromosuccinimide (NBS) to give a compound of Structure 3, which may further undergo a Suzuki coupling reaction with an arylamine substituted boric ester compound of Structure 4 as shown below to give final products. Scheme 1 is as follows,

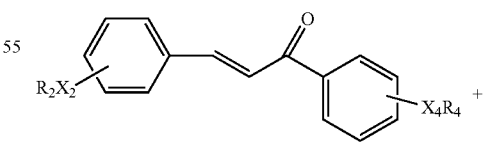

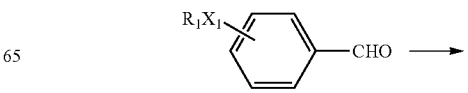

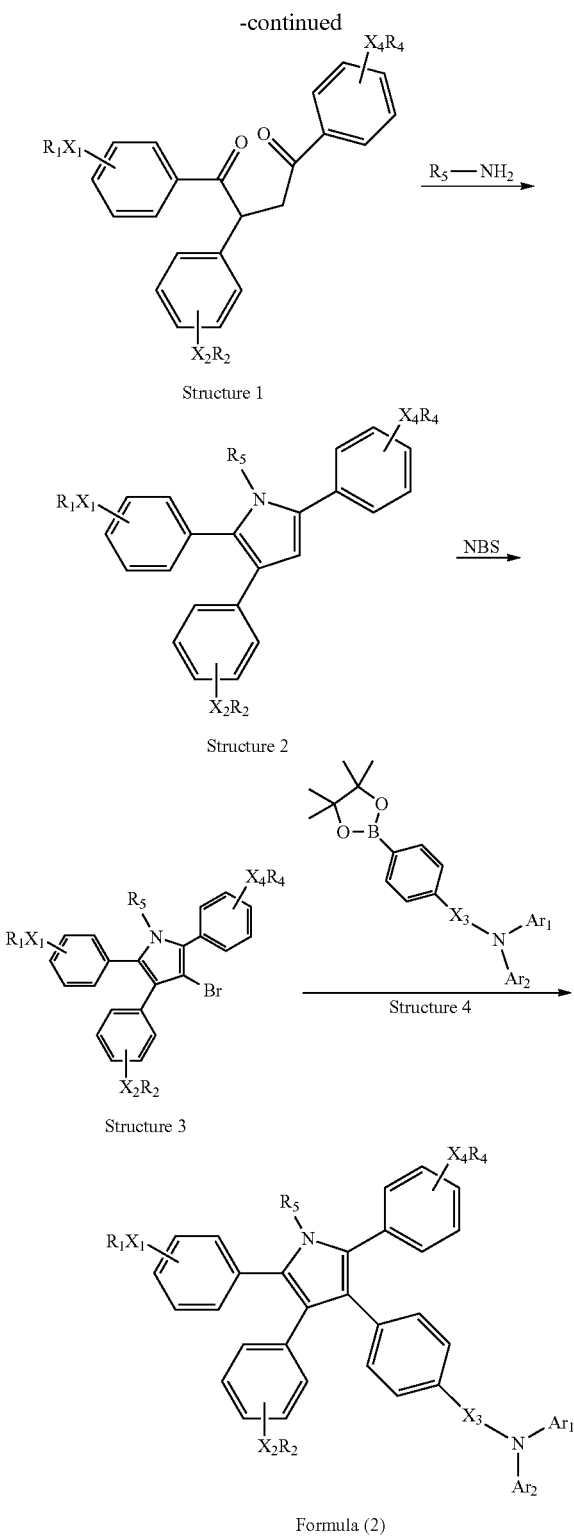

Structure 1

Structure 2

Structure 3

Formula (2)

wherein $R_1$, $R_2$, $R_4$, $R_5$, and $X_1$ through $X_4$ are as previously defined with reference to Formula (2).

The organic compound of the present invention may be used as charge transport layers and other organic layers in electronic devices, such as OLED devices. For example, the organic compound of the present invention may be used as charge blocking layers and charge generation layers.

The present invention also provides a film comprising at least one layer comprising the organic compound of the present invention described above.

The present invention also provides an electronic device comprising an organic layer comprising the organic compound of the present invention. The term "electronic device" herein refers to a device which depends on the principles of electronics and uses the manipulation of electron flow for its operation. The electronic device may include organic photovoltaic, organic field effect transistor, and a light emitting device such as OLED devices. The term "light emitting device" herein refers to a device that emits light when an electrical current is applied across two electrodes.

The organic device of the present invention may comprise a first electrode; a second electrode; and one or more organic layers interposed between the first electrode and the second electrode, wherein the organic layer comprises one or more organic compounds of the present invention. The organic layer can be a charge transfer layer that can transport charge carrying moieties, either holes or electrons. The organic layer may comprise a hole transport layer, an emissive layer, an electron transport layer, or a hole injection layer. Preferably, the organic layer is a hole transport layer or a hole injection layer. In addition to the organic compound of the present invention, the organic layer may comprise one or more dopants. "Dopant" refers to an electron acceptor or a donator that increases the conductivity of an organic layer of an organic electronic device, when added to the organic layer as an additive. Organic electronic devices may likewise be influenced, with regard to their electrical conductivity, by doping. The organic layer comprising the organic compound of the present invention may be prepared by evaporative vacuum deposition or solution process such as spin coating and ink-jet printing.

In the present invention, "aryl" refers to an organic radical derived from aromatic hydrocarbon by the removal of one hydrogen atom therefrom. An aryl group may be a monocyclic and/or fused ring system each ring of which suitably contains from 4 to 6, preferably from 5 or 6 atoms. Structures wherein two or more aryl groups are combined through single bond(s) are also included. Examples of aryls include phenyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl. The anthryl may be 1-anthryl, 2-anthryl or 9-anthryl. The fluorenyl may be any one of 1-fluorenyl, 2-fluorenyl, 3-fluorenyl, 4-fluorenyl and 9-fluorenyl.

In the present invention, "substituted aryl" refers to an aryl in which at least one hydrogen atom is substituted with a heteroatom or a chemical group containing at least one heteroatom. Heteroatoms may include, for example, O, N, P and S. The chemical group containing at least one heteroatom herein may include, for example, OR', NR'$_2$, PR'$_2$, P(=O)R'$_2$, SiR'$_3$; where each R' is a $C_1$-$C_{30}$ hydrocarbyl group.

In the present invention, "heteroaryl" refers to an aryl group, in which at least one carbon atom or CH group or $CH_2$ group is substituted with a heteroatom (for example, B, N, O, S, P(=O), Si and P) or a chemical group containing at least one heteroatom. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. Specific examples include, for example, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4, 3-b]benzofuranyl, benzothiophenyl, fluoreno[4, 3-b]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof.

In the present invention, "substituted heteroaryl" refers to a heteroaryl in which at least one hydrogen atom is substituted with a heteroatom or a chemical group containing at least one heteroatom. Heteroatoms may include, for example, O, N, P and S. The chemical group containing at least one heteroatom may include, for example, OR', NR'$_2$, PR'$_2$, P(=O)R'$_2$, or SiR'$_3$, wherein each R' is a C$_1$-C$_{30}$ hydrocarbyl group.

In the present invention, "hydrocarbyl" refers to a chemical group containing only hydrogen and carbon atoms.

In the present invention, "alkyl" and other substituents containing "alkyl" moiety include both linear and branched species. Examples of alkyls include methyl, ethyl, propyl, iso-propyl, butyl, iso-butyl, tert-butyl, pentyl, or hexyl.

In the present invention, "substituted alkyl" refers to an alkyl in which at least one hydrogen atom is substituted with a heteroatom or a chemical group containing at least one heteroatom. Heteroatoms may include, for example, O, N, P and S. The chemical group containing at least one heteroatom herein may include, for example, OR', NR'$_2$, PR'$_2$, P(=O)R'$_2$, or SiR'$_3$; where each R' is a C$_1$-C$_{30}$ hydrocarbyl group.

In the present invention, "cycloalkyl" includes a monocyclic hydrocarbon and a polycyclic hydrocarbon such as substituted or unsubstituted adamantyl or substituted or unsubstituted C$_7$-C$_{30}$ bicycloalkyl.

In the present invention, other substituted groups described above have one or more substituents. Substituents may include, for example, deuterium, halogen, C$_1$-C$_{30}$ alkyl with or without halogen substituent(s), C$_6$-C$_{30}$ aryl, C$_1$-C$_{30}$ heteroaryl with or without C$_6$-C$_{30}$ aryl substituent(s), a 5- to 7-membered heterocycloalkyl containing one or more heteroatom(s) selected from, for example, B, N, O, S, P(=O), Si and P, a 5 to 7-membered heterocycloalkyl fused with one or more aromatic ring(s), C$_3$-C$_{30}$ cycloalkyl, C$_5$-C$_{30}$ cycloalkyl fused with one or more aromatic ring(s), tri(C$_1$-C$_{30}$) alkylsilyl, di(C$_1$-C$_{30}$)alkyl(C$_6$-C$_{30}$)arylsilyl, tri(C$_6$-C$_{30}$)arylsilyl, adamantyl, C$_7$-C$_{30}$ bicycloalkyl, C$_2$-C$_{30}$ alkenyl, C$_2$-C$_{30}$ alkynyl, cyano, carbazolyl; BR$_6$R$_7$, PR$_8$R$_9$, or P(=O)R$_{10}$R$_{11}$, wherein R$_6$ through R$_{11}$ independently represent C$_1$-C$_{30}$ alkyl, C$_6$-C$_{30}$ aryl or C$_1$-C$_{30}$ heteroaryl; C$_1$-C$_{30}$ alkyloxy, C$_1$-C$_{30}$ alkylthio, C$_6$-C$_{30}$ aryloxy, C$_6$-C$_{30}$ arylthio, C$_1$-C$_{30}$ alkoxycarbonyl, C$_1$-C$_{30}$ alkylcarbonyl, C$_6$-C$_{30}$ arylcarbonyl, C$_6$-C$_{30}$ aryloxycarbonyl, C$_1$-C$_{30}$ alkoxycarbonyloxy, C$_1$-C$_{30}$ alkylcarbonyloxy, C$_6$-C$_{30}$ arylcarbonyloxy, C$_6$-C$_{30}$ aryloxycarbonyloxy, carboxyl, nitro and hydroxyl; or that the substituents are linked together to form a ring. For example, a substituent may form a ring structure with one or more atoms on the backbone molecule comprising said substituent.

EXAMPLES

The following examples illustrate embodiments of the present invention. All parts and percentages are by weight unless otherwise indicated.

All solvents and reagents were obtained from commercial vendors, and were used in the highest available purities, and/or when necessary, recrystallized before use. Dry solvents were obtained from an in-house purification/dispensing system (hexane, toluene, and tetrahydrofuran), or purchased from Sigma-Aldrich. All experiments involving "water sensitive compounds" were conducted in "oven dried" glassware, under nitrogen (N$_2$) atmosphere, or in a glovebox. Reactions were monitored by analytical thin-layer chromatography (TLC) on precoated aluminum plates (VWR 60 F254), visualized by UV light and/or potassium permanganate staining. Flash chromatography was performed on an ISCO COMBIFLASH system with GRACERESOLV cartridges.

| Material name | Chemical structure/Abbreviation | Supplier | CAS No. |
|---|---|---|---|
| Trans-chalcone | | Energy Chemical | 614-47-1 |
| Benzaldehyde | | Sinopharm Chemical Reagent Co., Ltd | 100-52-7 |
| Aniline | NH$_2$ | | 62-53-3 |

| Material name | Chemical structure/Abbreviation | Supplier | CAS No. |
| --- | --- | --- | --- |
| 3-ethyl-5-(2-hydroxyethyl)-4-methylthiazolium bromide | | | 54016-70-5 |
| N-([1,1'-biphenyl]-4-yl)-9,9-dimethyl-9H-fluoren-2-amine | | | 897671-69-1 |
| N-bromosuccinimide | NBS | | 128-08-5 |
| 2-(Dicyclohexylphosphino)-2',4',6'-triisopropylbiphenyl | X-Phos | | 564483-18-7 |
| Palladium acetate | Pd(OAc)$_2$ | | 3375-31-3 |
| [1,1'-Bis(diphenylphosphino)ferrocene]dichloropalladium (II) | Pd(dppf)$_2$Cl$_2$ | | 72287-26-4 |

The following standard analytical equipment and methods are used in the Examples.

Modeling

All computations utilized the Gaussian09 program as described in Gaussian 09, Revision A.02, Frisch, M. J. et al., Gaussian, Inc., Wallingford Conn., 2009. The calculations were performed with the hybrid density functional theory (DFT) method, B3LYP as described in Becke, A. D. J. Chem. Phys. 1993, 98, 5648; Lee, C. et al., Phys. Rev B 1988, 37, 785; and Miehlich, B. et al., Chem. Phys. Lett. 1989, 157, 200; and the 6-31G* (5d) basis set as described in Ditchfield, R. et al., J. Chem. Phys. 1971, 54, 724; Hehre, W. J. et al., J. Chem. Phys. 1972, 56, 2257; and Gordon, M. S. Chem. Phys. Lett. 1980, 76, 163. The singlet state calculations use the closed shell approximation, and the triplet state calculations use the open shell approximation. All values are quoted in eV. The HOMO and LUMO values are determined from the orbital energies of the optimized geometry of the singlet ground state. The triplet energies are determined as the difference between the total energy of the optimized triplet state and the optimized singlet state. A procedure, as described in Lin, B. C et al., J. Phys. Chem. A 2003, 107, 5241-5251, is applied to calculate the reorganization energy of each molecule, with which as the indicator of electron and hole mobility.

NMR $^1$H-NMR spectra (500 MHZ or 400 MHZ) are obtained on a Varian VNMRS-500 or VNMRS-400 spectrometer at 30° C. The chemical shifts are referenced to tetramethyl silane (TMS) (6:000) in CDCl$_3$.

Differential Scanning Calorimetry (DSC)

DSC measurements are carried out on a TA Instruments Q2000 instrument at a scan rate of 10° C./min under N$_2$ atmosphere for all cycles. The sample (about 7-10 mg) is scanned from room temperature (20-25° C.) to 300° C., cooled to −60° C., and reheated to 300° C. T$_g$ is measured on the second heating scan. Data analysis is performed using TA Universal Analysis software. The T$_g$ value is calculated using an "onset-at-inflection" methodology.

Thermal Gravimetric Analysis (TGA)

TGA measurements are carried out on a TA Instruments TGA-Q500 under N$_2$ atmosphere. The sample (about 7-10 mg) is weighed in a platinum standard plate and loaded into the instrument. The sample is first heated to 60.0° C. and equilibrated for 30 minutes to remove solvent residues in the sample. Then the sample is cooled to 30.0° C. The temperature is ramped from 30.0° C. to 600.0° C. with 10.0° C./min rate and the weight change is recorded to determine the decomposition temperature (T$_d$) of the sample. The temperature-weight % (T-Wt %) curve is obtained by TGA scan. The temperature at the 5% weight loss is determined as T$_d$.

Liquid Chromatography-Mass Spectrometry (LC/MS)

A sample is dissolved in tetrahydrofuran (THF) at around 0.6 mg/mL. 5 μL sample solution is injected on an Agilent 1220 HPLC/G6224A TOF mass spectrometer. The following analysis conditions are used:

Column: 4.6×150 mm, 3.5 m ZORBAX Eclipse Plus C$_{18}$; column temperature: 40° C.; Mobile phase: THF/deioned (DI) water=65/35 volume ratio (Isocratic method); Flow rate: 1.0 mL/min; and MS conditions: Capillary Voltage: 3500 kV (Pos); Mode: Pos; Scan: 100-2000 amu; Rate: 1 s/scan; and Desolvation temperature: 300° C.

High Performance Liquid Chromatography (HPLC)

A sample is dissolved in THF at around 0.6 mg/mL. The sample solution is at last filtrated through a 0.45 μm syringe filter and 5 μL of the filtrate is injected to HPLC system. The following analysis conditions are used:

Injection volume: 5 μL; Instrument: Agilent 1200 HPLC; Column: 4.6×150 mm, 3.5 m ZORBAX Eclipse Plus C$_{18}$; Column temperature: 40° C.; Detector: DAD=250, 280, 350 nm; Mobile Phase: THF/DI water=65/35 volume ratio (Isocratic method); and Flow rate: 1 mL/min.

Example (Ex) 1 Synthesis of HTL-1

Synthesis of Compound 1

To a mixture of chalcone (208 mg, 1.0 mmol), benzaldehyde (127.2 mg, 1.2 mmol), 3-ethyl-5-(2-hydroxyethyl)-4-methylthiazolium bromide (50.4 mg, 0.20 mmol) and K$_2$CO$_3$ (27.6 mg, 0.20 mmol) was added THF (5.0 mL) at room temperature. The reaction mixture was stirred for 12 hours at room temperature and then filtered. The obtained organic phase was distilled to remove solvents, and the residue was used in the next step without purification.

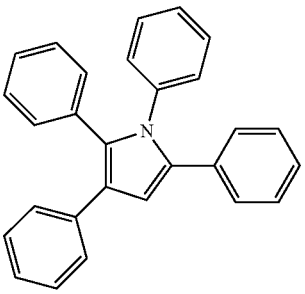

1

Synthesis of Compound 2

In a 100 mL three-neck flask equipped with a reflux condenser, NBS (178 mg, 1.0 mmol, 178 g/mol) was added to a solution of the Compound 1 obtained from above (371.5 mg, 1.0 mmol, 371.5 g/mol) in $CH_2Cl_2$/acetic acid (10 mL, 1:1) at 0° C. The reaction mixture was stirred at 0° C. for 0.5 hour. TLC was utilized to monitor the reaction. After the reaction completed, deionized (DI) water was added to quench the reaction. The resulting mixture was extracted with ethyl acetate (EtOAc). The resulting extracts were washed with water and brine, dried over anhydrous $Na_2SO_4$, and filtered. Solvents were removed under reduced pressure and the residue was recrystallized in ethyl alcohol (EtOH) to give Compound 2 with a yield of 90%. $^1$H NMR (400 MHz, $CDCl_3$, ppm): δ 7.27-7.32 (m, 4H), 7.22-7.24 (m, 6H), 7.09-7.13 (m, 3H), 7.02-7.08 (m, 3H), 6.90-6.92 (m, 4H). LC-MS-ESI (m/z): calculated mass for $C_{28}H_{20}BrN$: 449.08, found $(M+H)^+$: 450.0863.

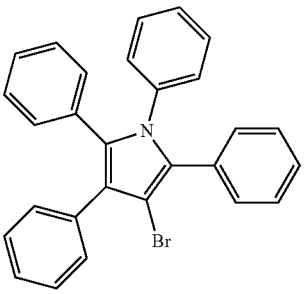

2

Synthesis of Compound 3

The Compound 3 was prepared by the following three steps:

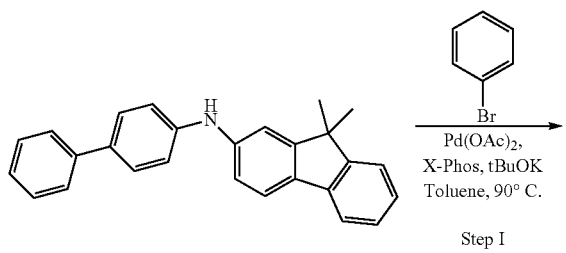

Step I

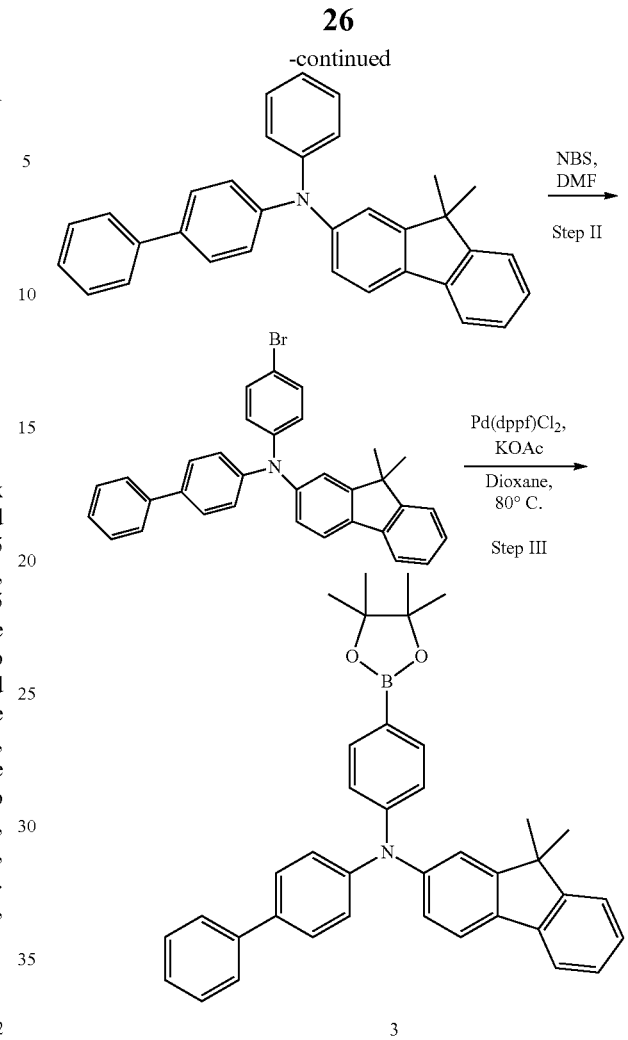

3

Step I: N-([1,1'-biphenyl]-4-yl)-9,9-dimethyl-9H-fluoren-2-amine (40.0 g, 110 mmol), bromobenzene (23.4 g, 150 mmol), $Pd(OAc)_2$ (616 mg, 2.75 mmol), X-Phos (1.57 g, 3.3 mmol), and tBuOK (24.6 g, 220 mmol) were added into a 250 mL three-neck round-bottom flask equipped with a reflux condenser. After addition of 250 mL dry toluene under $N_2$ atmosphere, the resultant suspension was heated to 90° C. and stirred for 12 hours under a flow of $N_2$. After cooling to room temperature, water was added and the organic layer was separated. Solvent in the organic layer was evaporated under vacuum and the residue was used for the next step without further purification.

Step II: To a solution of N-([1,1'-biphenyl]-4-yl)-9,9-dimethyl-N-phenyl-9H-fluoren-2-amine (35.0 g, 80 mmol) obtained from Step I above in 150 mL N,N-dimethylformamide (DMF), N-bromosuccinimide (NBS) (16.02 g, 90 mmol) in 100 mL DMF was added dropwise in 30 minutes. After addition, the mixture was stirred at room temperature for 12 hours, poured into water to precipitate, and then filtered. The resulting solid was recrystallized from dichloromethane (DCM) and ethanol to give white solid with a yield above 90%.

Step III: A mixture of the white solid obtained from Step II above (15.48 g, 30 mmol), 4,4,4',4',5,5,5',5'-octamethyl-2,2'-bi(1,3,2-dioxaborolane) (9.14 g, 36 mmol), $Pd(dppf)_2Cl_2$ (571 mg, 0.75 mmol), $CH_3COOK$ (4.41 g, 45 mmol), and 60 mL of dry dioxane was heated at 85° C. under $N_2$ atmosphere for 12 hours. After cooling to room temperature, solvent was removed under vacuum and then water was added. The resulting mixture was extracted with $CH_2Cl_2$. The resulting organic layer was collected and dried over anhydrous sodium sulphate. After filtration, the filtrate was evaporated to remove solvent and the residue was purified through silica gel column to give the Compound 3 as white solid with a yield above 90%.

Synthesis of HTL-1

To a mixture of the Compound 2 obtained above (450.3 mg, 1.0 mmol, 450.3 g/mol) and the Compound 3 obtained above (1.0 eq, 564 g/mol) in toluene (20 mL) was added $Pd(OAc)_2$ (5% mol, 11 mg), X-Phos (5% mol, 24 mg), and $K_3PO_4$ (2.0 mmol, 424 mg). The reaction mixture was stirred at reflux for about 12 hours under $N_2$ atmosphere. TLC was utilized to monitor the reaction. After the reaction completed, DI water was added to quench the reaction. The resulting mixture was extracted with EtOAc. The obtained extracts were washed with water and brine, dried over anhydrous $Na_2SO_4$, and filtered. Solvents were removed under reduced pressure and separated via silica gel column to give products as white solid powders with a yield of 85%. Multiple recrystalization of the powders in DCM/EtOH (1:4 volume, 10 mL), EtOH, and EtOAc gave the resultant products with a purity as high as 99.5% as determined by HPLC. $^1$H NMR (400 MHz, $CDCl_3$, ppm): δ 7.54-7.65 (m, 5H), 7.45-7.51 (m, 2H), 7.34-7.41 (m, 5H), 7.28-7.34-6.93 (m, 4H), 7.04-7.24 (m, 15H), 6.89-7.01 (m, 7H), 6.71-6.86 (m, 2H), 1.41 (s, 6H). LC-MS-ESI (m/z): calculated mass for $C_{61}H_{46}N_2$: 806.37, found $(M+H)^+$: 807.3757. The structure of HTL-1 obtained is shown as follows.

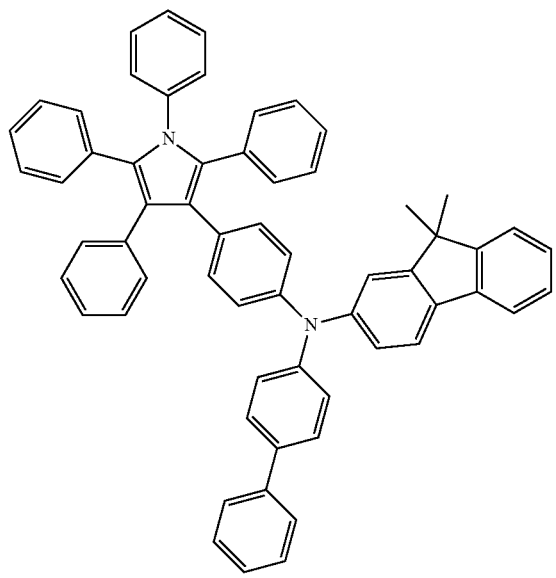

HTL-1

HTL-1 obtained above has a HOMO level of −4.63 eV, a LUMO level of −0.84 eV, a triplet energy of 2.60 eV, and a hole mobility level of 0.23, as determined by the modeling method described above.

Thermal properties of HTL-1 were analyzed by DSC and TGA and results are shown in Table 1. As shown in Table 1, HTL-1 has a $T_g$ of 141.6° C. and a $T_d$ of 385.7

TABLE 1

| Sample Name | $T_d$ [° C.] | $T_g$ [° C.] | $T_m$ [° C.] |
|---|---|---|---|
| HTL-1 | 385.7 | 141.6 | N/A* |

*No obvious melting point ($T_m$), as measured by DSC, was observed.

Ex 2 and Comparative (Comp) Ex A OLED Device Fabrication

All organic materials were purified by sublimation before deposition. OLEDs were fabricated onto an ITO (Indium Tin Oxide) coated glass substrate that served as the anode, and topped with an aluminum cathode. All organic layers were thermally deposited by chemical vapor deposition, in a vacuum chamber with a base pressure of <$10^{-7}$ torr. The deposition rates of organic layers were maintained at 0.1~0.05 nm/s. The aluminum cathode was deposited at 0.5 nm/s. The active area of the OLED device was "3 mm×3 mm," as defined by the shadow mask for cathode deposition.

Each cell, containing HIL (hole injection layer), HTL, EML (electron emission layer), ETL, and EIL (electron injection layer), based on materials described in Table 2, was placed inside a vacuum chamber, until it reached $10^{-6}$ torr. To evaporate each material, a controlled current was applied to the cell, containing the material, to raise the temperature of the cell. An adequate temperature was applied to keep the evaporation rate of the materials constant throughout the evaporation process.

For the HIL layer, N4,N4-diphenyl-N4,N4'-bis(9-phenyl-9H-carbazol-3-yl)-[1,1'-biphenyl]-4,4'-diamine was evaporated at a constant 1 Å/s rate, until the thickness of the layer reached 600 Angstrom. Simultaneously, the HTL-1 compound was evaporated at a constant 1 A/s rate, until the thickness reached 200 Angstrom. The N4,N4'-di(naphthalen-1-yl)-N4,N4'-diphenyl-[1,1'-biphenyl]-4,4'-diamine (NPB) was used as a reference material to compare with the inventive HTL-1.

For the EML layer, 9,10-di(naphthalen-2-yl)anthracene (ADN, host) and (E)-9,9-dimethyl-7-(4-(naphthalen-2-yl (phenyl)amino) styryl)-N,N-diphenyl-9H-fluoren-2-amine (dopant) were co-evaporated, until the thickness reached 350 Angstrom. The deposition rate for host material was 1.0 A/s, and the deposition for the dopant material was 0.02 A/s, resulting in a 2% doping of the host material.

For the ETL layer, tris(8-hydroxyquinolinato)aluminum (Alq3) was evaporated at a constant 1 A/s rate, until the thickness reached 200 Angstrom. Finally, "20 Angstrom" of a thin electron injection layer (Liq) was evaporated at a 0.5 A/s rate.

The current-voltage-brightness (J-V-L) characterizations for the OLED devices were performed with a source measurement unit (KEITHLY 238) and a luminescence meter (MINOLTA CS-100A). Electroluminescence spectra of the OLED devices were collected by a calibrated CCD spectrograph. The results are shown in Table 3 below.

TABLE 2

| | Name | Abbreviation | CAS number |
|---|---|---|---|
| Hole Injection Material | N4,N4-diphenyl-N4,N4'-bis(9-phenyl-9H-carbazol-3-yl)-[1,1'-biphenyl]-4,4'-diamine | | 887402-92-8 |
| Hole Transport | Comp Ex A: N4,N4'-di(naphtalen-1-yl)-N4,N4'-diphenyl-[1,1'- | NPB | 123847-85-8 |

TABLE 2-continued

| Name | | Abbreviation | CAS number |
|---|---|---|---|
| Material Ex 2: HTL-1 | biphenyl]-4,4'-diamine | | |
| Fl Blue Host | 9,10-di(naphthalen-2-yl)anthracene | ADN | 122648-99-1 |
| Fl Blue Dopant | (E)-9,9-dimethyl-7-(4-(naphthalen-2-yl(phenyl)amino)styryl)-N,N-diphenyl-9H-fluoren-2-amine | | 1228810-33-0 |
| Electron Transport Material | tris(8-hydroxyquinolinato)aluminum | Alq3 | 2085-33-8 |
| Electron Injection Material | lithium quinolate | Liq | 850918-68-2 |

As shown in Table 3, the inventive OLED device containing an HTL film layer containing HTL-1 showed lower driving voltage and higher luminous efficiency (8% higher), as compared to the OLED device containing the comparative HTL materials (Comp Ex A).

TABLE 3

| Device | HTL Material | Voltage @ 1000 nit [V] | Luminous Efficiency @ 1000 nit [Cd/A (candela per ampere)] | CIE* (X, Y) |
|---|---|---|---|---|
| Comp Ex A | NPB | 6.7 | 6.1 | 0.148, 0.148 |
| Ex 2 | HTL-1 | 6.5 | 6.6 | 0.147, 0.148 |

*CIE refers to International Commission on Illumination.

What is claimed is:

1. An organic compound having the structure represented by Formula (1):

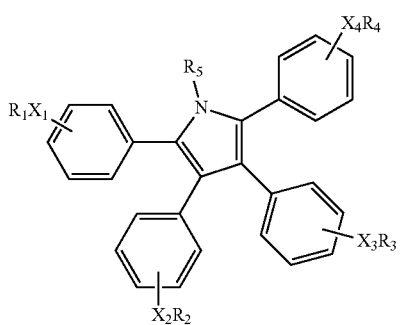

Formula (1)

wherein $X_1$ through $X_4$ are each independently a chemical bond, or each independently selected from the group consisting of a substituted or unsubstituted $C_6$-$C_{60}$ arylene and a substituted or unsubstituted $C_1$-$C_{60}$ heteroarylene; and $X_1$ through $X_4$ may each independently form fused rings with the phenyl rings they are bonded to;

$R_1$ through $R_4$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{50}$ arylthio, a substituted or unsubstituted $C_1$-$C_{60}$ heteroaryl, a halogen, a cyano, a hydroxyl, a carbonyl, and an amino group substituted with a substituted or unsubstituted $C_6$-$C_{60}$ aryl or a substituted or unsubstituted $C_1$-$C_{60}$ heteroaryl; and only one of $R_1$ through $R_4$ is an amino group having the structure

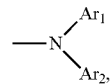

wherein $Ar_1$ and $Ar_2$ are each independently selected from the group consisting of a substituted or unsubstituted $C_6$-$C_{60}$ aryl and a substituted or unsubstituted $C_1$-$C_{60}$ heteroaryl; and $R_5$ is selected from the group consisting of hydrogen, deuterium, a substituted or unsubstituted $C_1$-$C_{50}$ alkyl, a substituted or unsubstituted $C_1$-$C_{50}$ alkoxycarbonyl, a substituted or unsubstituted $C_6$-$C_{60}$ aryl, and a substituted or unsubstituted $C_1$-$C_{60}$ heteroaryl.

2. The organic compound of claim 1, wherein the organic compound has the structure represented by Formula (2):

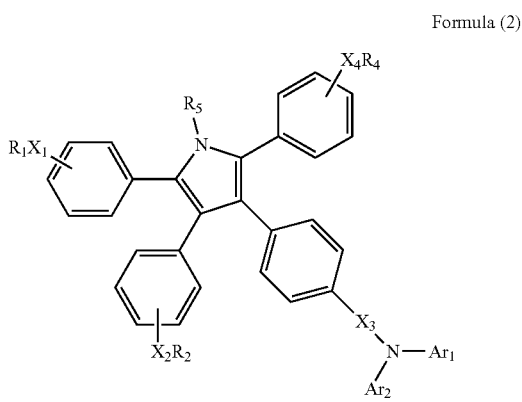

Formula (2)

wherein $Ar_1$ and $Ar_2$ are each independently selected from the group consisting of a substituted or unsubstituted $C_6$-$C_{60}$ aryl and a substituted or unsubstituted $C_1$-$C_{60}$ heteroaryl;

$R_1$, $R_2$ and $R_4$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{50}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl;

$R_5$ is selected from the group consisting of hydrogen, deuterium, a substituted or unsubstituted $C_1$-$C_{50}$ alkyl, a substituted or unsubstituted $C_1$-$C_{50}$ alkoxycarbonyl, a substituted or unsubstituted $C_6$-$C_{60}$ aryl, and a substituted or unsubstituted $C_1$-$C_{60}$ heteroaryl; and $X_1$ through $X_4$ are each independently a chemical bond, or each independently selected from the group consisting of a substituted or unsubstituted $C_6$-$C_{60}$ arylene and a substituted or unsubstituted $C_1$-$C_{60}$ heteroarylene; and $X_1$ through $X_4$ may each independently form fused rings with the phenyl rings they are bonded to.

3. The organic compound of claim 1, wherein the organic compound has the structure represented by Formula (3):

Formula (3)

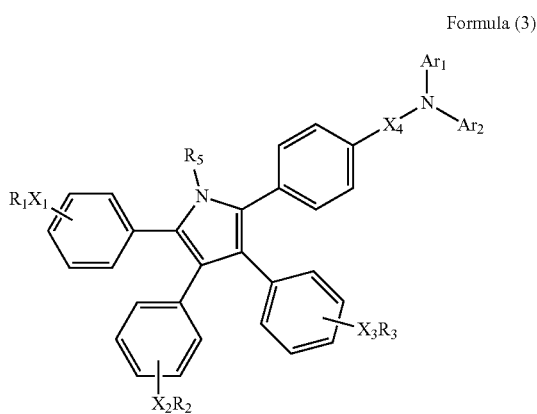

wherein Ar₁ and Ar₂ are each independently selected from the group consisting of a substituted or unsubstituted $C_6$-$C_{60}$ aryl and a substituted or unsubstituted $C_1$-$C_{60}$ heteroaryl; and R₁, R₂, and R₃ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl;

R₅ is selected from the group consisting of hydrogen, deuterium, a substituted or unsubstituted $C_1$-$C_{50}$ alkyl, a substituted or unsubstituted $C_1$-$C_{50}$ alkoxycarbonyl, a substituted or unsubstituted $C_6$-$C_{60}$ aryl, and a substituted or unsubstituted $C_1$-$C_{60}$ heteroaryl; and X₁ through X₄ are each independently a chemical bond, or each independently selected from the group consisting of a substituted or unsubstituted $C_6$-$C_{60}$ arylene and a substituted or unsubstituted $C_1$-$C_{60}$ heteroarylene; and X₁ through X₄ may each independently form fused rings with the phenyl rings they are bonded to.

4. The organic compound of claim 1, wherein the organic compound has the structure represented by Formula (4):

Formula (4)

wherein Ar₁ and Ar₂ are each independently selected from the group consisting of a substituted or unsubstituted $C_6$-$C_{60}$ aryl and a substituted or unsubstituted $C_1$-$C_{60}$ heteroaryl;

X₃ is a chemical bond, or selected from the group consisting of a substituted or unsubstituted $C_6$-$C_{60}$ arylene and a substituted or unsubstituted $C_1$-$C_{60}$ heteroarylene; and X₃ may form fused rings with the phenyl ring it is bonded to; and R₅ is selected from the group consisting of hydrogen, deuterium, a substituted or unsubstituted $C_1$-$C_{50}$ alkyl, a substituted or unsubstituted $C_1$-$C_{50}$ alkoxycarbonyl, a substituted or unsubstituted $C_6$-$C_{60}$ aryl, and a substituted or unsubstituted $C_1$-$C_{60}$ heteroaryl.

5. The organic compound of claim 1, wherein the organic compound has the structure represented by Formula (4-I):

Formula (4-I)

wherein Ar₁ and Ar₂ are each independently selected from the group consisting of a substituted or unsubstituted $C_6$-$C_{60}$ aryl and a substituted or unsubstituted $C_1$-$C_{60}$ heteroaryl;

X₄ is a chemical bond, or selected from the group consisting of a substituted or unsubstituted $C_6$-$C_{60}$ arylene and a substituted or unsubstituted $C_1$-$C_{60}$ heteroarylene; and X₄ may form fused rings with the phenyl ring it is bonded to; and R₅ is selected from the group consisting of hydrogen, deuterium, a substituted or unsubstituted $C_1$-$C_{50}$ alkyl, a substituted or unsubstituted $C_1$-$C_{50}$ alkoxycarbonyl, a substituted or unsubstituted $C_6$-$C_{60}$ aryl, and a substituted or unsubstituted $C_1$-$C_{60}$ heteroaryl.

6. The organic compound of claim 1, wherein the structure is selected from the following structures (5-1) through (5-9);

(5-1)

(5-2) 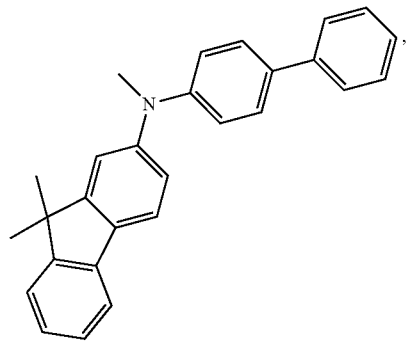
(5-3) 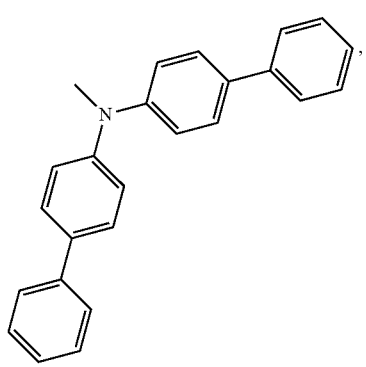
(5-4) 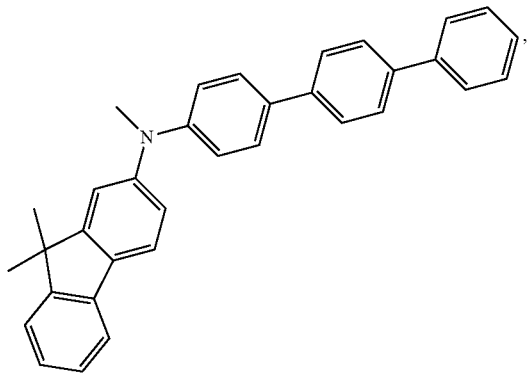
(5-5) 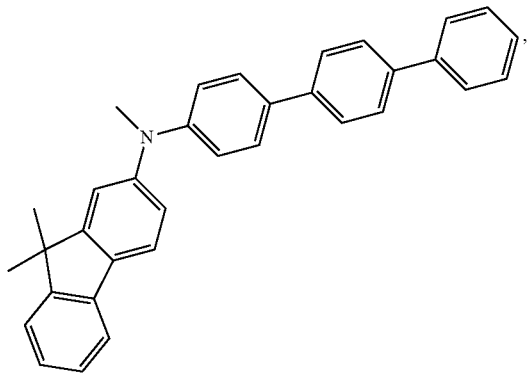
(5-6) 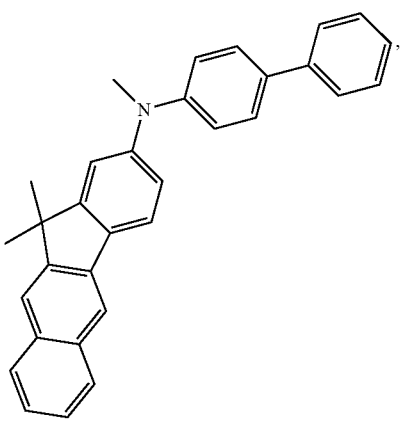
(5-7) 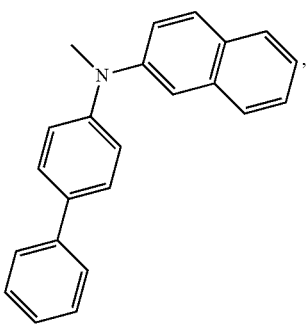
(5-8) 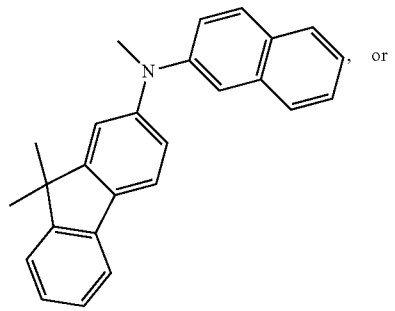
(5-9) 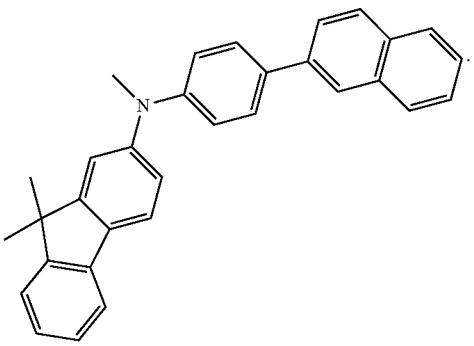
7. The organic compound of claim 1, wherein $R_5$ is selected from the group consisting of: —$CH_3$, —$CH_2CH_3$,
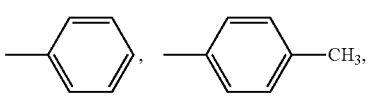

-continued
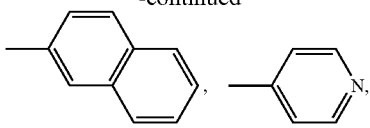
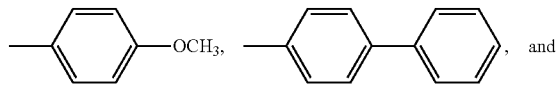
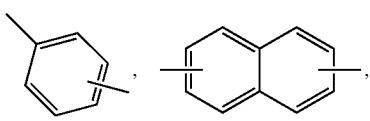
8. The organic compound of claim 1, wherein $X_1$ through $X_4$ are each independently selected from a chemical bond,
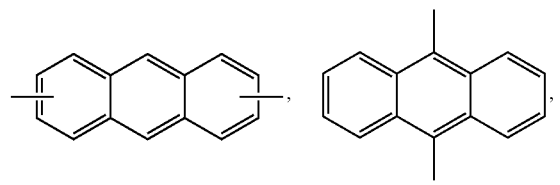
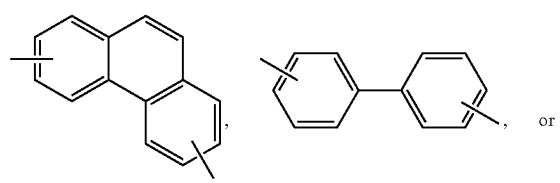
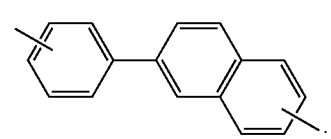
9. The organic compound of claim 1, wherein the organic compound is selected from the following structures:
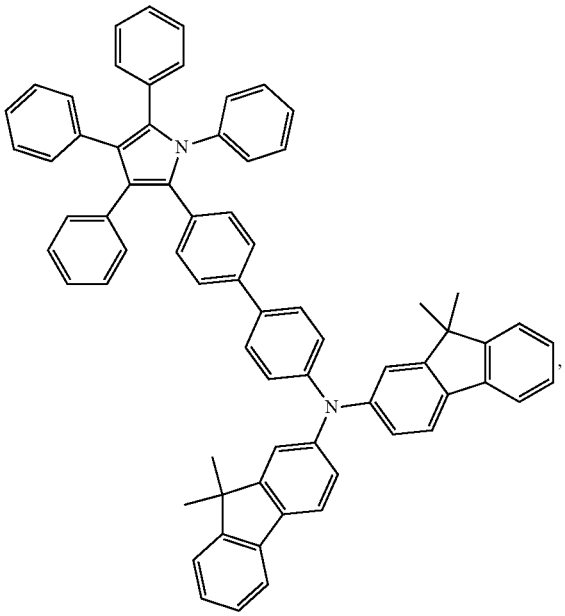
(1)
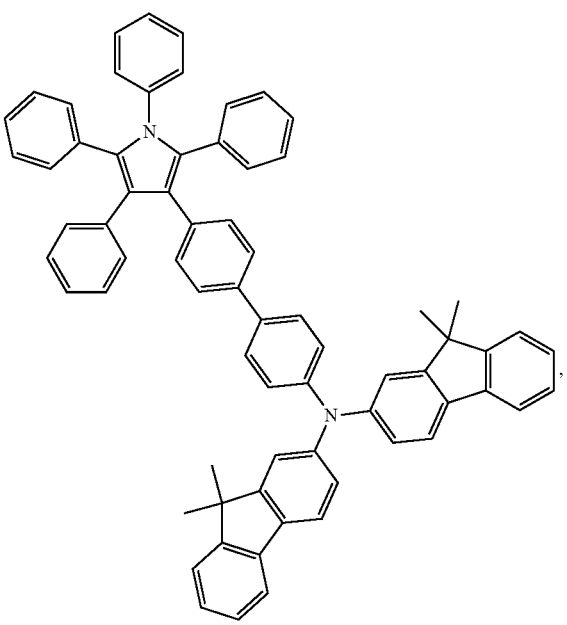
(2)

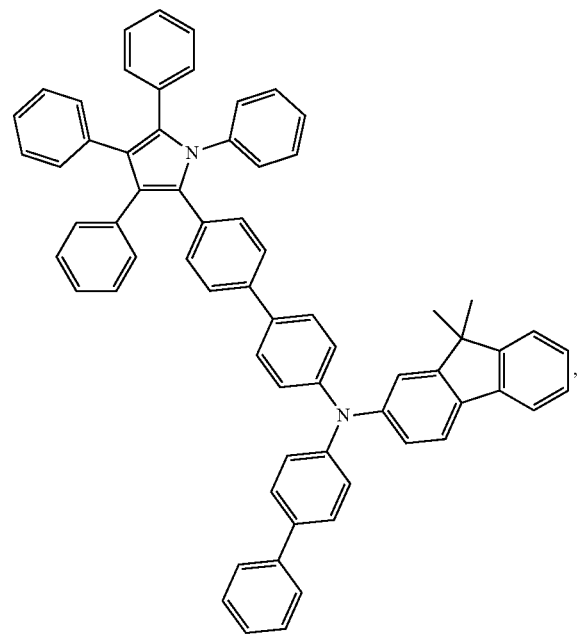
(3)
(4)
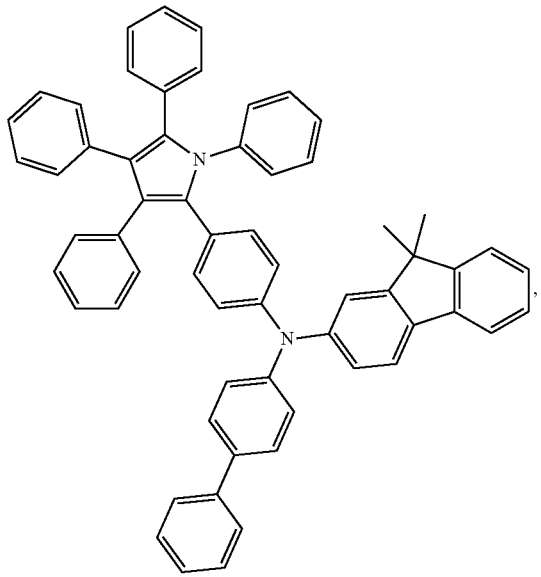
(5)
(6)

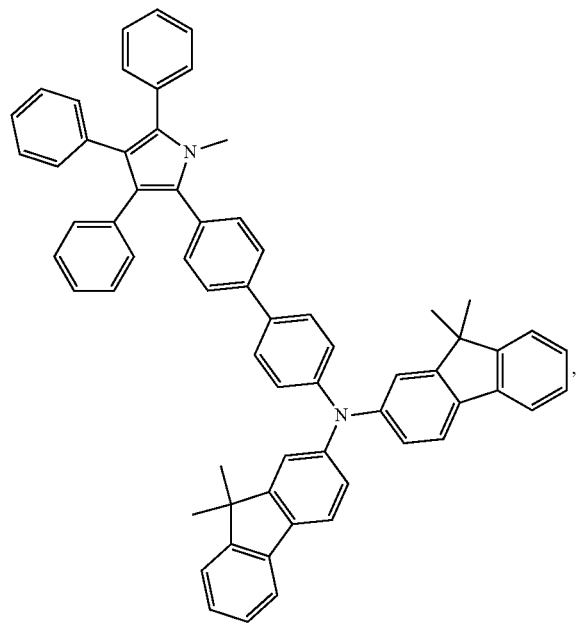
(7)
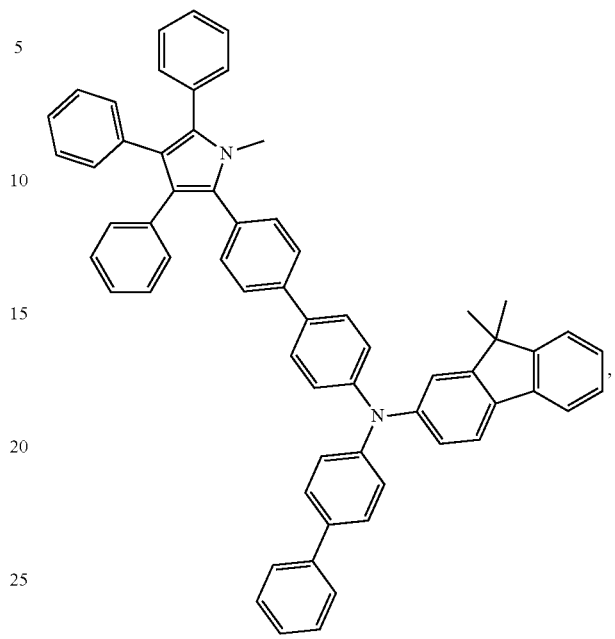
(9)
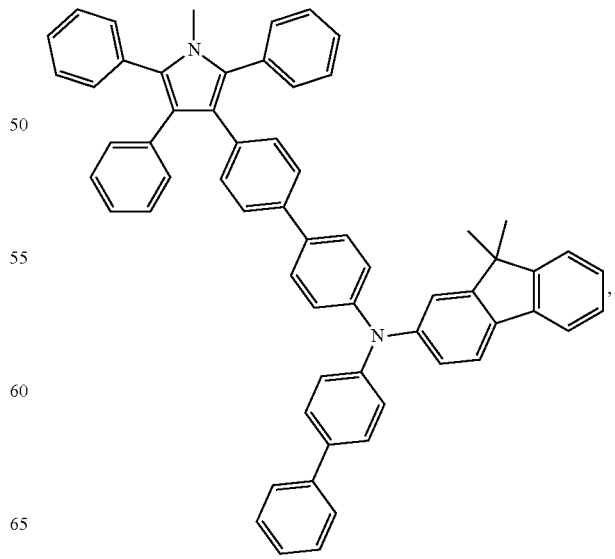
(8)
(10)

(11)
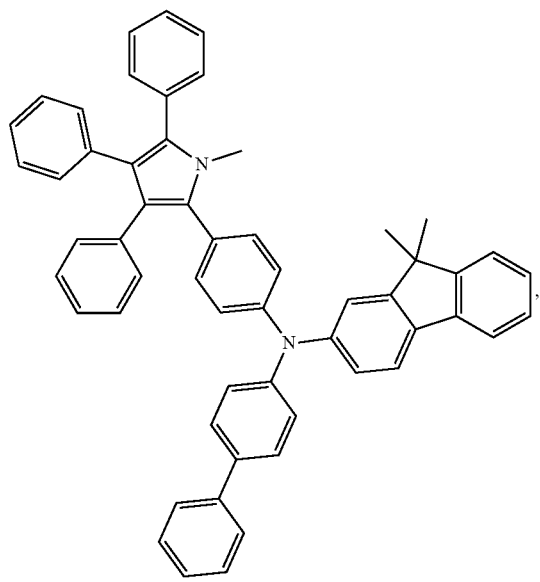
(12)
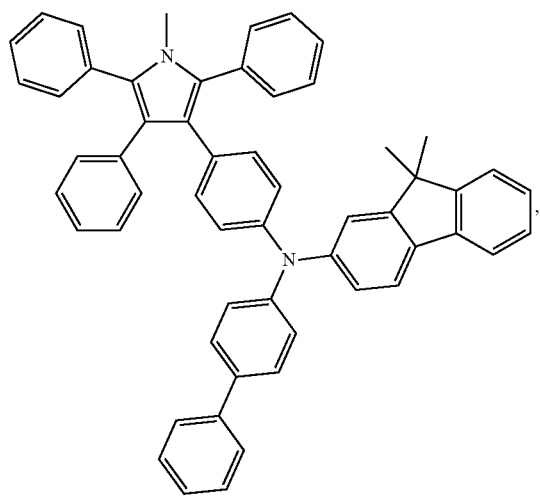
(13)
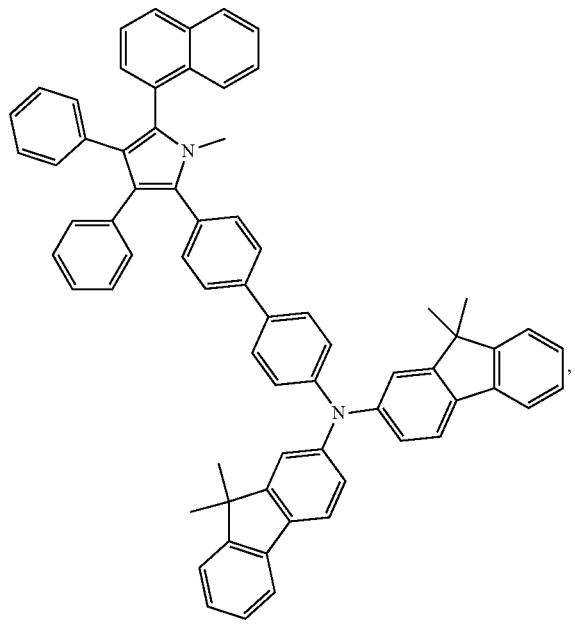
(14)
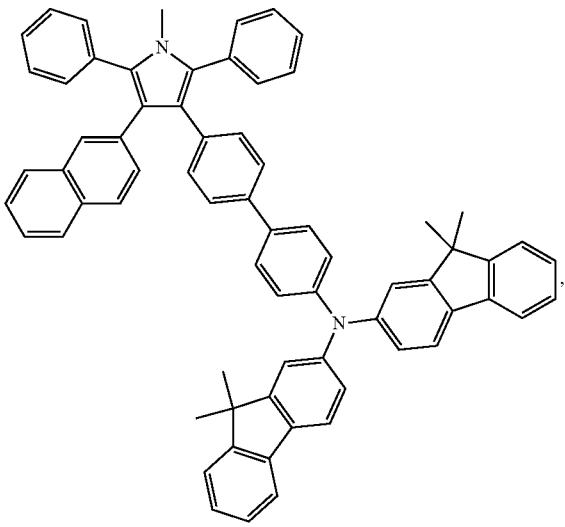

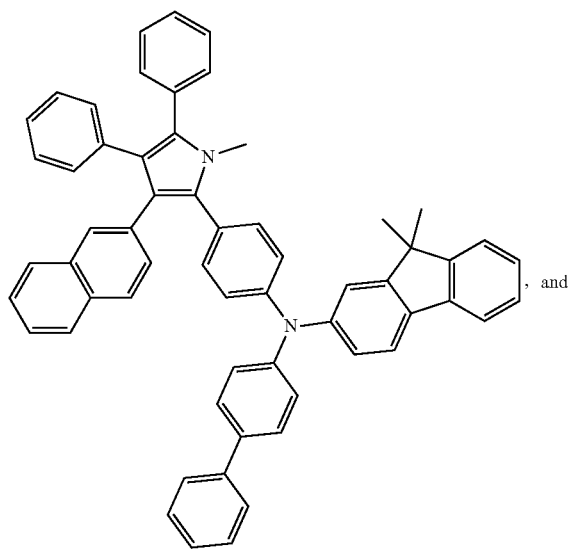
, and

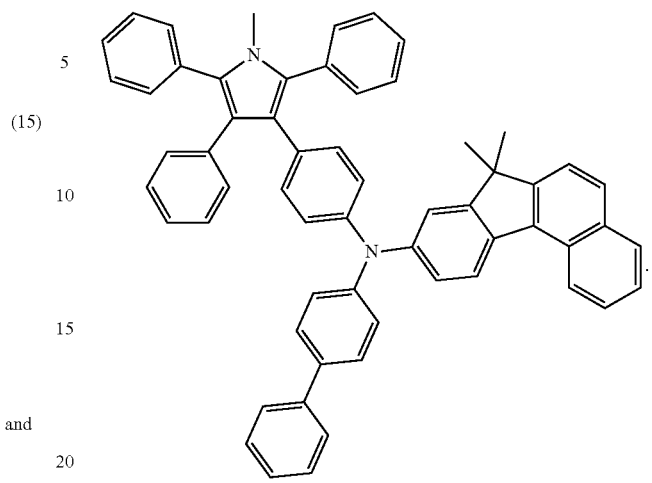

10. An electronic device comprising an organic layer, wherein the organic layer comprises the organic compound of claim 1.

11. The electronic device of claim 10, wherein the organic layer comprises a hole transport layer, an emissive layer, an electron transport layer, or a hole injection layer.

12. The electronic device of claim 11, wherein the electronic device is a light emitting device.

* * * * *